US011571185B2

(12) United States Patent
Son et al.

(10) Patent No.: US 11,571,185 B2
(45) Date of Patent: Feb. 7, 2023

(54) MEDICAL IMAGE DISPLAYING APPARATUS AND METHOD OF DISPLAYING MEDICAL IMAGE USING THE SAME

(71) Applicant: SAMSUNG MEDISON CO., LTD., Gangwon-do (KR)

(72) Inventors: Yuri Son, Seongnam-si (KR); Junsung Park, Seongnam-si (KR); Yeongseon Kim, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 145 days.

(21) Appl. No.: 17/091,814

(22) Filed: Nov. 6, 2020

(65) Prior Publication Data
US 2021/0137500 A1    May 13, 2021

Related U.S. Application Data

(60) Provisional application No. 62/932,631, filed on Nov. 8, 2019.

(30) Foreign Application Priority Data

Mar. 19, 2020    (KR) .................. 10-2020-0034045

(51) Int. Cl.
A61B 8/08       (2006.01)
G06T 7/13       (2017.01)
(Continued)

(52) U.S. Cl.
CPC .............. A61B 8/5269 (2013.01); A61B 8/14 (2013.01); A61B 8/463 (2013.01); A61B 8/523 (2013.01);
(Continued)

(58) Field of Classification Search
None
See application file for complete search history.

(56) References Cited

U.S. PATENT DOCUMENTS 8,867,808 B2    10/2014   Satoh et al.
9,710,910 B2 *   7/2017   Kim .................. G06V 10/20
(Continued)

FOREIGN PATENT DOCUMENTS

JP    3878456 B2    2/2007
JP    3878462 B2    2/2007
(Continued)

OTHER PUBLICATIONS

International Search Report dated Feb. 15, 2021 issued in International Patent Application No. PCT/KR2020/015490.

Primary Examiner — Amelie R Davis
Assistant Examiner — Marjan Saboktakin
(74) Attorney, Agent, or Firm — Morgan, Lewis & Bockius LLP

(57) ABSTRACT

Provided are a medical image displaying apparatus and a medical image displaying method for registering an ultrasound image with a previously obtained medical image and outputting a result of the registration, the medical image displaying method including: transmitting ultrasound signals to an object and receiving ultrasound echo signals from the object via an ultrasound probe of the medical image displaying apparatus; obtaining a first ultrasound image based on the ultrasound echo signals; performing image registration between the first ultrasound image and a first medical image that is previously obtained; obtaining a second ultrasound image of the object via the ultrasound probe; obtaining a second medical image by transforming the first medical image to correspond to the second ultra-
(Continued)

sound image; and displaying the second medical image together with the second ultrasound image.

14 Claims, 15 Drawing Sheets

(51) Int. Cl.
  *A61B 8/00* (2006.01)
  *A61B 8/14* (2006.01)
  *G06T 7/33* (2017.01)
  *G16H 30/40* (2018.01)
  *G16H 30/20* (2018.01)
  *G16H 50/20* (2018.01)

(52) U.S. Cl.
  CPC .............. *A61B 8/5246* (2013.01); *A61B 8/54* (2013.01); *G06T 7/13* (2017.01); *G06T 7/33* (2017.01); *G16H 30/20* (2018.01); *G16H 30/40* (2018.01); *G16H 50/20* (2018.01); *A61B 8/4444* (2013.01); *G06T 2200/04* (2013.01); *G06T 2207/10132* (2013.01); *G06T 2207/20084* (2013.01)

(56) References Cited

U.S. PATENT DOCUMENTS

| | | |
|---|---|---|
| 2016/0098621 A1 | 4/2016 | Tahmasebi Maraghoosh et al. |
| 2019/0008480 A1* | 1/2019 | Gerard ................. A61B 8/5246 |
| 2019/0237186 A1* | 8/2019 | El-Baz ..................... G06T 7/33 |
| 2020/0268348 A1* | 8/2020 | Park ..................... A61B 8/5261 |
| 2021/0042878 A1* | 2/2021 | Ghose ................. A61B 8/5261 |

FOREIGN PATENT DOCUMENTS

| | | |
|---|---|---|
| JP | 4750429 B2 | 8/2011 |
| JP | 2018-153455 A | 10/2018 |
| KR | 10-1118549 A | 2/2012 |
| KR | 10-1227272 B1 | 1/2013 |
| KR | 10-2015-0026354 A | 3/2015 |
| KR | 10-2016-0038405 A | 4/2016 |
| KR | 10-2016-0076868 A | 7/2016 |
| WO | 2017/202795 A1 | 11/2017 |

* cited by examiner

MEDICAL IMAGE DISPLAYING APPARATUS AND METHOD OF DISPLAYING MEDICAL IMAGE USING THE SAME

CROSS-REFERENCE TO RELATED APPLICATION(S)

This application is based on and claims the benefit of U.S. Provisional Patent Application No. 62/932,631, filed on Nov. 8, 2019, in the United States Patent and Trademark Office, and claims priority under 35 U.S.C. § 119 to Korean Patent Application No. 10-2020-0034045, filed on Mar. 19, 2020, in the Korean Intellectual Property Office, the disclosures of which are incorporated herein by reference in their entirety.

BACKGROUND

1. Field

Embodiments of the disclosure relate to medical image displaying apparatuses and methods of displaying medical images using the same.

2. Description of Related Art

Ultrasound diagnostic apparatuses transmit ultrasound signals generated by transducers of a probe to an object and detect information about signals reflected from the object, thereby obtaining at least one image of an internal part, for example, soft tissue or blood flow, of the object.

Ultrasound imaging apparatuses are compact and affordable and are capable of displaying images in real-time. Furthermore, as they are very safe due to lack of radiation exposure, such ultrasound imaging apparatuses have been widely used together with other types of diagnostic imaging apparatuses such as an X-ray diagnostic apparatus, a computed tomography (CT) scanner, a magnetic resonance imaging (MRI) apparatus, a nuclear medicine diagnostic apparatus, etc.

Because ultrasound images have a low signal-to-noise ratio (SNR), the limitation may be compensated through image registration with CT images or MR images. Image registration is performed by extracting features from an ultrasound image and a CT/MR image and matching the extracted features to each other.

However, when a shape of an organ is deformed or its position is moved by an ultrasound probe, it is difficult to easily perform image registration.

SUMMARY

Provided are medical image displaying apparatuses and medical image displaying methods for registering an ultrasound image with a previously obtained medical image and outputting a result of the registration.

Additional aspects will be set forth in part in the description which follows and, in part, will be apparent from the description, or may be learned by practice of the presented embodiments of the disclosure.

In accordance with an aspect of the disclosure, a medical image displaying method includes: transmitting ultrasound signals to an object and receiving ultrasound echo signals from the object via an ultrasound probe of a medical image displaying apparatus; obtaining a first ultrasound image based on the ultrasound echo signals; performing image registration between the first ultrasound image and a first medical image that is previously obtained; obtaining a second ultrasound image of the object via the ultrasound probe; obtaining a second medical image by transforming the first medical image to correspond to the second ultrasound image; and displaying the second medical image together with the second ultrasound image.

In accordance with another aspect of the disclosure, a medical image displaying apparatus includes: a display; an ultrasound probe configured to transmit ultrasound signals to an object and receive ultrasound echo signals from the object; a memory storing one or more instructions; and a processor configured to execute the one or more instructions to: obtain a first ultrasound image based on the ultrasound echo signals; perform image registration between the first ultrasound image and a first medical image that is previously obtained; control the ultrasound probe to obtain a second ultrasound image of the object; obtain a second medical image by transforming the first medical image to correspond to the second ultrasound image; and control the display to display the second medical image together with the second ultrasound image.

In accordance with another aspect of the disclosure, a computer-readable recording medium has recorded thereon a program for executing, on a computer, at least one of the medical image displaying methods according to the presented embodiments of the disclosure.

An application stored in the recording medium may be intended to execute functions according to at least one of the medical image displaying methods of the presented embodiments of the disclosure.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
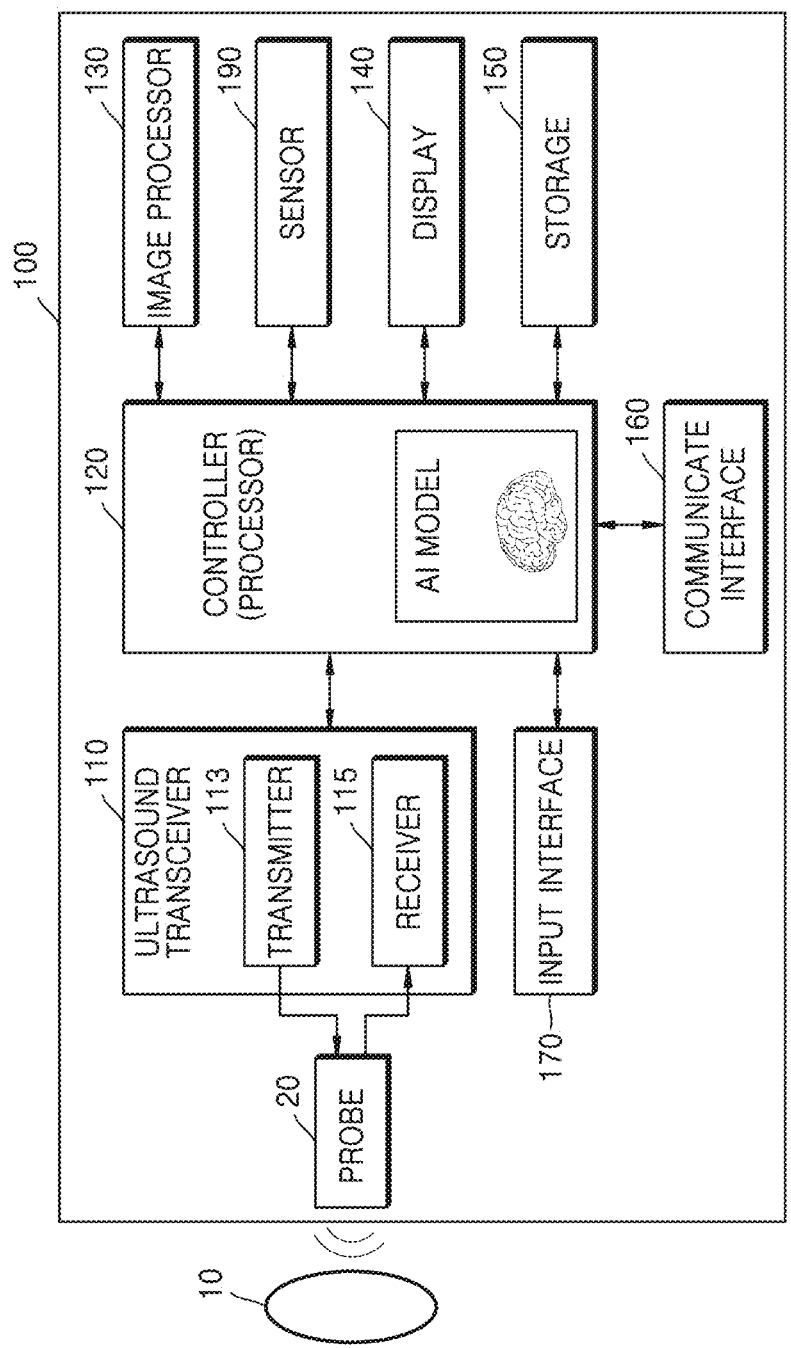
FIG. 1 is a block diagram illustrating an ultrasound diagnosis apparatus according to an exemplary embodiment.

The present specification describes principles of the disclosure and sets forth embodiments thereof to clarify the scope of claims of the disclosure and to allow those of ordinary skill in the art to implement the embodiments of the disclosure. The embodiments of the disclosure may have different forms.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

Expressions such as "at least one of," when preceding a list of elements, modify the entire list of elements and do not modify the individual elements of the list.

Some embodiments of the disclosure may be described in terms of functional block components and various processing operations. Some or all of such functional blocks may be implemented by any number of hardware and/or software components that perform specific functions. For example, functional blocks of the disclosure may be implemented by one or more microprocessors or by circuit components for performing certain functions. For example, functional blocks according to the disclosure may be implemented with any programming or scripting language. The functional blocks may be implemented using various algorithms executed on one or more processors. Furthermore, the disclosure may employ techniques of the related art for electronics configuration, signal processing and/or data processing. The terms "mechanism", "element", "means", and "construction" are used in a broad sense and are not limited to mechanical or physical embodiments.

Throughout the specification, it will be understood that when a part is referred to as being "connected" or "coupled" to another part, it can be "directly connected" to or "electrically coupled" to the other part with one or more intervening elements interposed therebetween. Throughout the specification, when a part "includes" or "comprises" an element, unless there is a particular description contrary thereto, the part may further include other elements, not excluding the other elements.

Furthermore, connecting lines or connectors shown in various figures are intended to represent exemplary functional relationships and/or physical or logical couplings between components in the figures. In an actual device, connections between components may be represented by alternative or additional functional relationships, physical connections, or logical connections.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

In the present specification, a medical image displaying apparatus is an electronic apparatus capable of outputting at least one of a medical image stored therein, a medical image received via a network, and a medical image obtained from an object.

For example, a medical image displaying apparatus may include a medical imaging apparatus such as an ultrasound imaging apparatus capable of obtaining ultrasound images. Alternatively, a medical image displaying apparatus may include a computing device such as a general-purpose computer (e.g., a PC) and a mobile device (e.g., a smartphone, a tablet personal computer (PC), etc.), which output a medical image obtained from a server (e.g., a medical image transmission system such as a picture archiving and communication system (PACS)) via a network.

According to an embodiment, image registration presented in the specification may be performed using a visual understanding technique of AI technology.

AI technologies consist of machine learning (deep learning) technology using algorithms for autonomously classifying/learning features of input data and element technologies for simulating functions of a human brain such as cognition and decision-making by using machine learning algorithms. In the fields of AI, visual understanding is a technology for recognizing and processing an object in the same way as performed by a human visual system, and includes object recognition, object tracking, image retrieval, person recognition, scene understanding, spatial understanding, image enhancement, etc.

According to the disclosure, functions related to AI may operate via a processor and a memory. The processor may be configured as one or a plurality of processors. In this case, the one or plurality of processors may be a general-purpose processor such as a central processing unit (CPU), an application processor (AP), or a digital signal processor (DSP), a dedicated graphics processor such as a graphical processing unit (GPU) or a vision processing unit (VPU), or a dedicated AI processor such as a neural processing unit (NPU). The one or plurality of processors control input data to be processed according to predefined operation rules or an AI model stored in the memory. Alternatively, when the one or more processors are a dedicated AI processor, the dedicated AI processor may be designed with a hardware structure specialized for processing a particular AI model.

The predefined operation rules or AI model may be created via a training process. This means that the predefined operation rules or AI model set to perform desired characteristics (or purpose) are created by training a basic AI model on a large number of training data via a learning algorithm. The training process may be performed by an apparatus itself in which AI is performed or via a separate server and/or system. Examples of a learning algorithm may include, but are not limited to, supervised learning, unsupervised learning, semi-supervised learning, and reinforcement learning.

An AI model may be composed of a plurality of neural network layers. Each of the neural network layers has a plurality of weight values and may perform neural network computations via calculations between a result of computations in a previous layer and a plurality of weight values. A plurality of weight values assigned to each of the neural network layers may be optimized by a result of training the AI model. For example, a plurality of weight values may be modified to reduce or minimize a loss or cost value acquired by the AI model during a training process. An artificial neural network may include a deep neural network (DNN) and may be, for example, a convolutional neural network (CNN), a DNN, a recurrent neural network (RNN), a restricted Boltzmann machine (RBM), a deep belief network (DBN), a bidirectional recurrent DNN (BRDNN), or deep Q-networks (DQN) but is not limited thereto.

An AI model presented herein may be created by learning a plurality of text data and image data input as training data according to predefined criteria. The AI model may generate resultant data by performing learned functions in response to input data and output the resultant data.

Furthermore, the AI model may include a plurality of AI models trained to perform at least one function.

According to an embodiment, an AI model may be built in a medical image displaying apparatus. The medical image displaying apparatus may perform registration between an ultrasound image and a CT/MR image by using an AI model and display registered images.

According to an embodiment, a medical image displaying apparatus may transmit an obtained medical image to an electronic apparatus (e.g., a server) in which an AI model is built, and output a medical image by using data received from the electronic apparatus.

For example, the medical image displaying apparatus may transmit an ultrasound image obtained from an object to a server, receive a CT/MR image registered with an ultrasound image from the server, and display a resulting CT/MR image.

It will be understood that, although the terms including an ordinal number such as "first", "second", etc. may be used herein to describe various elements, these elements should not be limited by the terms. The terms are used to distinguish one element from another element.

Hereinafter, embodiments will be described in detail with reference to the accompanying drawings.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

Furthermore, the controller 120 may include an AI model 125 that registers an ultrasound image with a medical image from a different modality.

The AI model 125 may be trained to identify whether a condition for performing image registration between the ultrasound image and the medical image are satisfied and output a result of the identification.

The AI model 125 may be trained to obtain features in the ultrasound image and perform image registration by comparing and matching the obtained features with corresponding features in the medical image.

The AI model 125 may be trained to perform a correction operation on the medical image by comparing the features in the ultrasound image and with the corresponding features in the medical image. The AI model 125 may be trained to perform a shape correction on the medical image by applying a result of the correction operation to the medical image.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

A sensor 190 may include at least one sensor capable of obtaining information about a position of the probe 20. For example, the sensor 190 may include a magnetic field generator for generating a magnetic field within a certain range, an electromagnetic sensor for detecting electromagnetic induction in the magnetic field, and a position tracker for tracking a position of the electromagnetic sensor.

An example of the ultrasound diagnosis apparatus 100 according to the present exemplary embodiment is described below with reference to FIGS. 2A, 2B, and 2C.

Figure 2A:
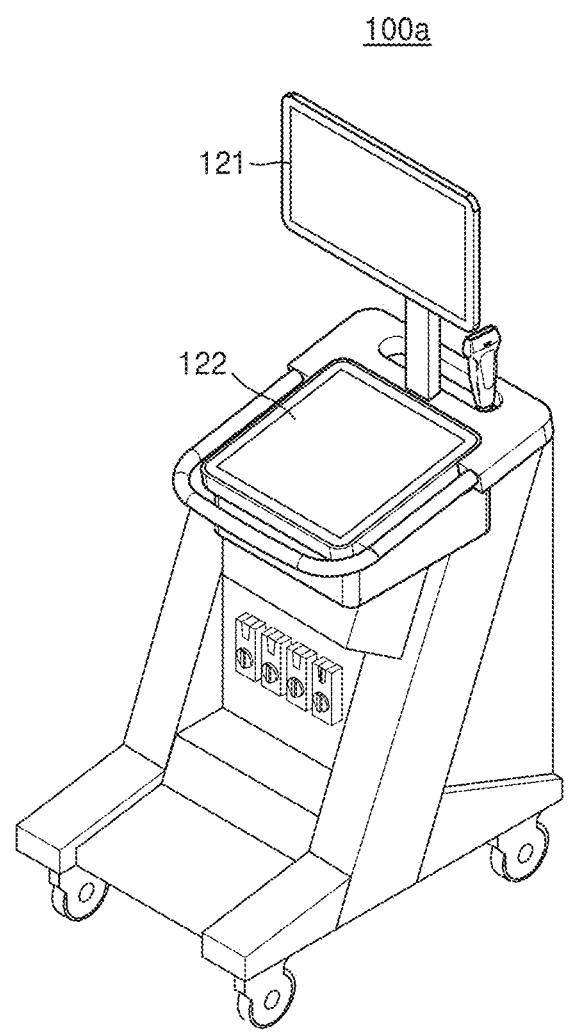
FIGS. 2A, 2B, and 2C are diagrams respectively illustrating an ultrasound diagnosis apparatus according to an exemplary embodiment.
Figure 2B:
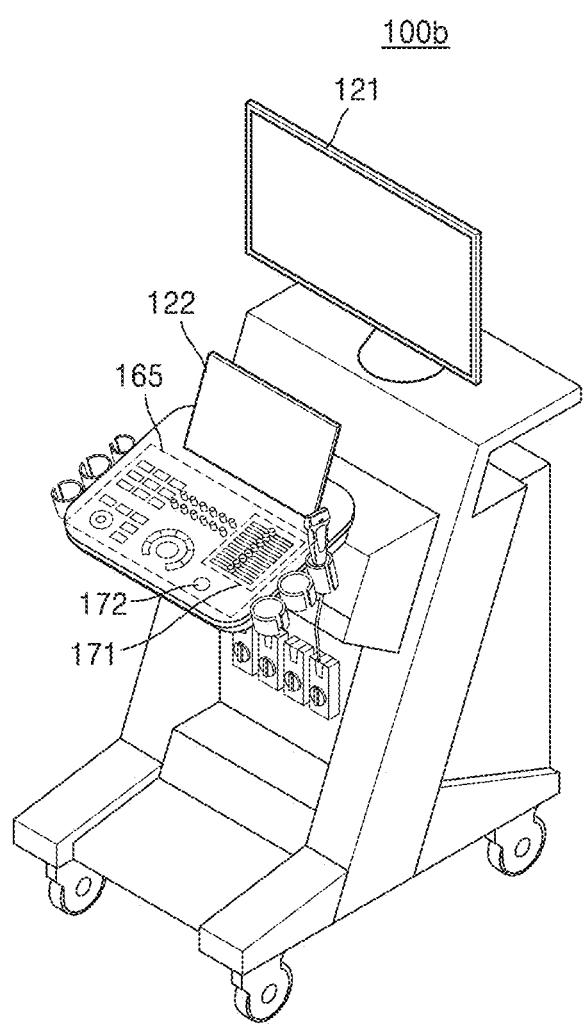
Figure 2C:
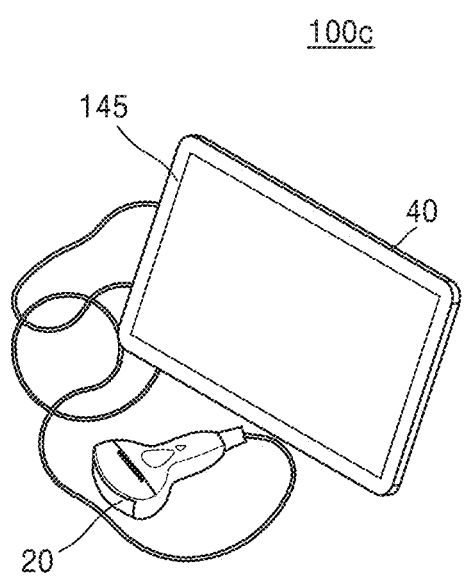

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
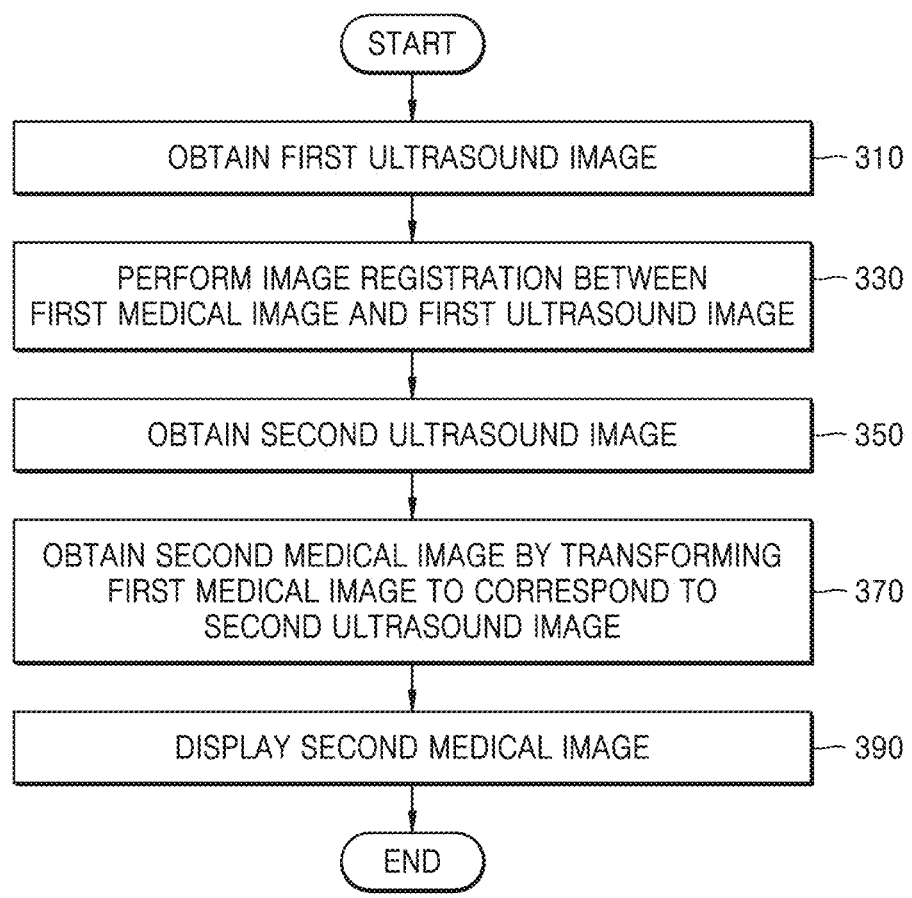
FIG. 3 is a flowchart of a method by which a medical image displaying apparatus outputs a medical image, according to an embodiment.

FIG. 3 is a flowchart of a method by which a medical image displaying apparatus outputs a medical image, according to an embodiment.

The medical image displaying apparatus may obtain a first ultrasound image (operation 310).

According to an embodiment, the medical image displaying apparatus may obtain an ultrasound image via the probe 20 connected thereto.

For example, the medical image displaying apparatus may be the ultrasound diagnosis apparatus 100. The ultrasound diagnosis apparatus 100 may transmit ultrasound signals to an object 10 and receive ultrasound echo signals from the object 10. The ultrasound diagnosis apparatus 100 may obtain an ultrasound image based on the ultrasound echo signals.

According to an embodiment, the medical image displaying apparatus may obtain an ultrasound image from at least one of an ultrasound diagnosis apparatus and a server via the communicator 160.

For example, the medical image displaying apparatus may receive, from an ultrasound diagnosis apparatus connected via a network, ultrasound image data obtained by the ultrasound diagnosis apparatus. As another example, the medical image displaying apparatus may receive ultrasound image data from a server, e.g., a medical image transmission system such as a PACS.

The medical image displaying apparatus may perform image registration between the first ultrasound image obtained in operation 310 and a first medical image (operation 330).

According to an embodiment, the first medical image may be a previously obtained medical image.

According to an embodiment, the first medical image may be an image stored in a memory of the medical image displaying apparatus.

According to an embodiment, the first medical image may be a medical image received by the medical image displaying apparatus from a server, e.g., a medical image transmission system such as a PACS.

According to an embodiment, the first medical image may be at least one of a CT image, an MR image, and a three-dimensional (3D) ultrasound image. Alternatively, the first medical image may be at least one of an X-ray image and a two-dimensional (2D) ultrasound image.

The medical image displaying apparatus may perform image registration by applying at least one of the first ultrasound image and the first medical image to an AI model.

According to an embodiment, the medical image displaying apparatus may obtain features in the first ultrasound image by applying the first ultrasound image to the AI model.

For example, the medical image displaying apparatus may apply the first ultrasound image to an AI model built therein. Alternatively, the medical image displaying apparatus may apply the first ultrasound image to an AI model by transmitting data regarding the first ultrasound image to a server on which the AI model is built.

The AI model may identify features in the first ultrasound image by analyzing the first ultrasound image applied thereto. The AI model may also identify an object in the first ultrasound image based on the features in the first ultrasound image.

According to an embodiment, the medical image displaying apparatus may perform image registration between the first ultrasound image and the first medical image by comparing and matching features in the first ultrasound image with corresponding features in the first medical image.

For example, the medical image displaying apparatus may identify and match corresponding features from among the features in the first ultrasound image and the features in the first medical image by using the AI model built therein.

Moreover, the features in the first medical image may be previously obtained. Alternatively, the features in the first medical image may be obtained by applying the first medical image to the AI model built in the medical image displaying apparatus.

According to an embodiment, the medical image displaying apparatus may transmit the first ultrasound image to a server and perform image registration by matching corresponding features from among the features in the first ultrasound image received from the server and the features in the first medical image. In this case, the server may obtain the features in the first ultrasound image by applying the first ultrasound image to the AI model built on the server.

According to an embodiment, the medical image displaying apparatus may transmit the first ultrasound image and the first medical image to the server and perform image registration by matching the features in the first ultrasound image with the features in the first medical image, which are received from the server. In this case, the server may obtain the features from the first ultrasound image by applying the first ultrasound image to the AI model built on the server. Furthermore, the server may obtain the features from the first medical image by applying the first medical image to the AI model built on the server.

According to an embodiment, the medical image displaying apparatus may transmit the first ultrasound image and the first medical image to the server and receive data for performing image registration (e.g., location information of the features in the first ultrasound image and the location information of the features in the first medical image) from the server. The medical image displaying apparatus may perform image registration between the first medical image and the first ultrasound image by using the data received from the server.

The medical image displaying apparatus may obtain a second ultrasound image (operation 350).

According to an embodiment, the medical image displaying apparatus may obtain an ultrasound image via the probe 20 connected to the medical image displaying apparatus.

According to an embodiment, the medical image displaying apparatus may obtain an ultrasound image from at least one of an ultrasound diagnosis apparatus and a server via the communicator 160.

According to an embodiment, the second ultrasound image may be an ultrasound image newly obtained as the probe 20 moves. In this case, the medical image displaying apparatus may obtain the second ultrasound image in which a shape of the object is changed as the probe 20 presses the object.

A repeated description with respect to operation 310 are omitted to avoid redundancy.

The medical image displaying apparatus may obtain a second medical image by transforming the first medical image to correspond to the second ultrasound image (operation 370).

According to an embodiment, the medical image displaying apparatus may obtain features in the second ultrasound image by applying the second ultrasound image to an AI model.

For example, the medical image displaying apparatus may apply the second ultrasound image to an AI model built on the medical image displaying apparatus. Alternatively, the medical image displaying apparatus may apply the second ultrasound image to an AI model by transmitting data regarding the second ultrasound image to the server on which the AI model is built.

The AI model may recognize features in the second ultrasound image. The AI model may identify an object in the second ultrasound image based on the features in the second ultrasound image.

According to an embodiment, the AI model may identify a difference between the second ultrasound image and the first medical image by comparing the features in the second ultrasound image with the features in the first medical image.

For example, the AI model may identify a difference between the second ultrasound image and the first medical image by respectively comparing locations of the features in the second ultrasound image with locations of the features in the first medical image. Furthermore, the AI model may compare locations of the features in the second ultrasound image with those of the features in the first medical image to thereby obtain first information regarding a change in a location of matching features in the second ultrasound image and the first medical image.

According to an embodiment, the AI model may obtain a second medical image by transforming the first medical image based on the matching features in the second ultrasound image and the first medical image.

For example, the AI model may obtain a second medical image by moving the features in the first medical image such that they correspond to the locations of the features in the second ultrasound image. In this case, the AI model may move the features in the first medical image by applying the first information to the features in the first medical image. The second medical image may be generated by moving the features in the first medical image.

According to an embodiment, the AI model may identify a difference between the first and second ultrasound images by comparing the features in the first ultrasound image with the features in the second ultrasound image.

For example, the AI model may track an object in the second ultrasound image by respectively comparing locations of the features in the first ultrasound image with locations of the features in the second ultrasound image.

As another example, the AI model may compare locations of the features in the first ultrasound image with those of the features in the second ultrasound image to thereby obtain second information regarding a change in a location of matching features in the first and second ultrasound images.

According to an embodiment, the AI model may obtain a second medical image by transforming the first medical image based on the matching features in the first and second ultrasound images.

For example, the AI model may move the features in the first medical image by applying the second information to the features in the first medical image. The second medical image may be generated by moving the features in the first medical image. In this case, the second information may be applied to the features in the first medical image because the image registration is performed in operation 330 to match the features in the first ultrasound image to the corresponding features in the first medical image.

The medical image displaying apparatus may obtain a second medical image from an AI neural network. For example, an AI neural network built in the medical image displaying apparatus may store the second medical image in the memory of the medical image displaying apparatus. As another example, an AI neural network built on the server may transmit the second medical image to the medical image displaying apparatus over the network.

The medical image displaying apparatus may display the second medical image (operation 390).

According to an embodiment, the medical image displaying apparatus may display the second medical image together with the second ultrasound image.

According to an embodiment, the medical image displaying apparatus may display the second medical image after performing image processing such that an object in the second ultrasound image and the second medical image may be easily identified.

For example, the medical image displaying apparatus may perform image processing to color-code the object. Alternatively, the medical image displaying apparatus may perform image processing to indicate a boundary of the object in a predefined color.

Figure 4:
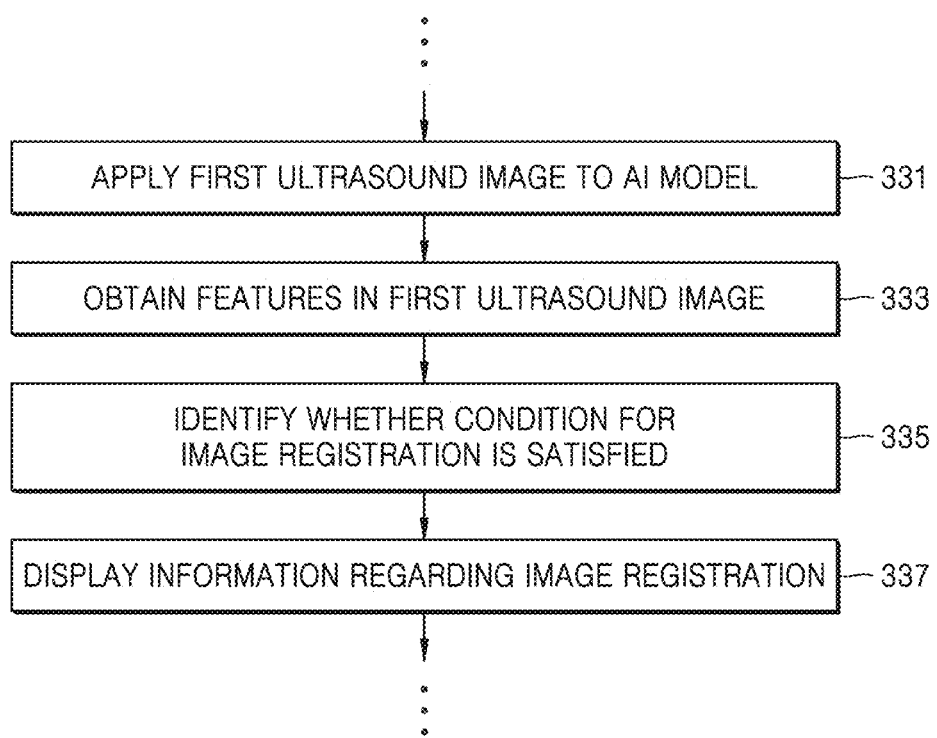
FIG. 4 is a flowchart of a method by which a medical image displaying apparatus registers an ultrasound image with a medical image, according to an embodiment.

FIG. 4 is a flowchart of a method by which a medical image displaying apparatus registers an ultrasound image with a medical image, according to an embodiment.

The medical image displaying apparatus may apply a first ultrasound image to the AI model (125 of FIG. 1) (operation 331).

Because the method of applying a first ultrasound image to an AI model, which has been described above with reference to operation 330, may be analogically applied in operation 331, a repeated description thereof will be omitted here.

The AI model 125 may obtain features in the first ultrasound image (operation 333).

The AI model 125 may be trained to obtain features from an ultrasound image by learning a plurality of ultrasound images, each including an object (e.g., the prostate, liver, kidneys, etc.), as training data.

According to an embodiment, the AI model 125 may be trained to obtain a boundary of an object (e.g., the prostate, liver, kidneys, etc.) as a feature.

According to an embodiment, the AI model 125 may be trained to obtain, as a feature, Euclidean distance used in semantic segmentation that classifies each of an ultrasound image and a medical image in pixel-wise manner.

The AI model 125 may obtain the Euclidean distance away from a boundary of the object to each image pixel.

According to an embodiment, the AI model 125 may be trained to identify a boundary of the object and obtain a distance map image indicating the Euclidean distance away from the boundary of the object, as described in more detail below with reference to FIG. 5.

According to an embodiment, the AI model 125 may output the obtained features in the first ultrasound image to the medical image displaying apparatus.

The medical image displaying apparatus may identify whether a condition for image registration is satisfied (operation 335).

According to an embodiment, the medical image displaying apparatus may identify whether a condition for image registration is satisfied based on the features in the first ultrasound image, which are obtained in operation 333.

For example, the medical image displaying apparatus may identify a total width of the object based on a boundary of the object and identify whether a condition for image registration is satisfied based on a ratio of a width of the object in the first ultrasound image to the identified total width of the object, as described in more detail below with reference to FIGS. 6 and 7.

As another example, the medical image displaying apparatus may identify whether a condition for image registration is satisfied based on a proportion of the object occupying the first ultrasound image, as described in more detail below with reference to FIG. 8.

As another example, the medical image displaying apparatus may identify whether a condition for image registration is satisfied based on a direction in which an ultrasound signal transmitted from a probe is oriented, as described in more detail below with reference to FIG. 9.

The medical image displaying apparatus may display information regarding the image registration (operation 337).

According to an embodiment, the medical image displaying apparatus may display information regarding whether the condition for image registration is satisfied.

For example, the medical image displaying apparatus may display information indicating that a proportion of an object being displayed in an ultrasound image is less than a certain percentage value.

As another example, the medical image displaying apparatus may display information indicating that a size of an object in an ultrasound image is less than a preset size.

As another example, the medical image displaying apparatus may display information indicating that an ultrasound signal is not being transmitted to an object.

According to an embodiment, the medical image displaying apparatus may display information regarding whether a shape of a registered medical image has been corrected, as described in more detail below with reference to FIGS. 6 and 7.

Figure 5:
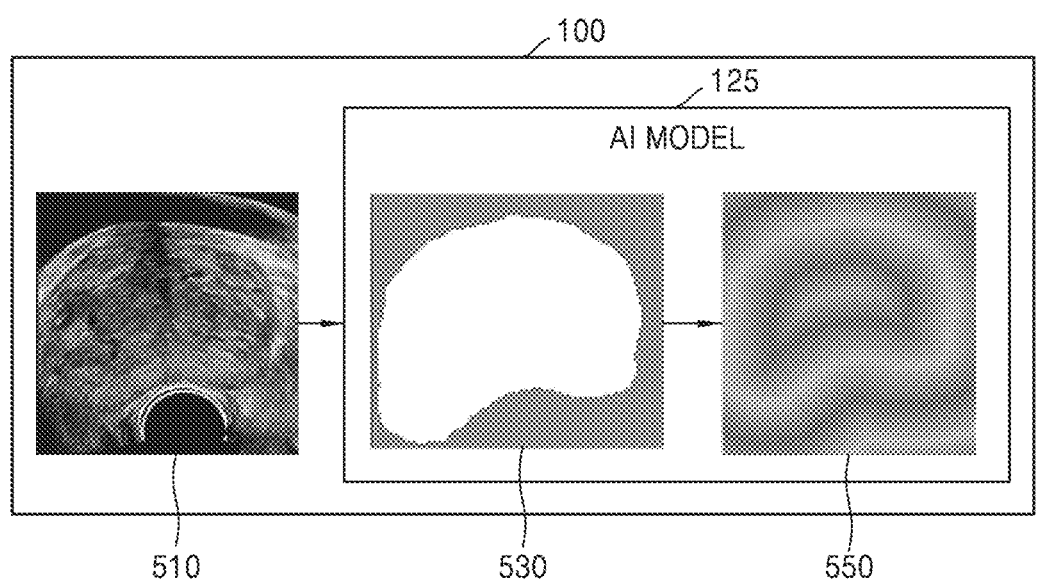
FIG. 5 illustrates an example in which a medical image displaying apparatus applies an ultrasound image to an artificial intelligence (AI) model, according to an embodiment.

FIG. 5 illustrates an example in which a medical image displaying apparatus applies an ultrasound image to an AI model, according to an embodiment.

Referring to FIG. 5, the medical image displaying apparatus may apply an ultrasound image 510 to an AI model 125.

According to an embodiment, the AI model 125 may be built in the medical image displaying apparatus. Alternatively, the AI model 125 may be built on a server connected to the medical image displaying apparatus via a network. An embodiment in which the AI model 125 is built in the medical image displaying apparatus is described for convenience. It is obvious to those of ordinary skill in the art that details of the AI model 125 described below may be analogically applied to an AI model according to other embodiments of the disclosure.

According to an embodiment, the AI model 125 may be trained to obtain features from an ultrasound image by learning a plurality of ultrasound images, each including an object, as training data.

For example, a plurality of ultrasound images, each including the prostate, may be input to the AI model 125 as training data. Each of the ultrasound images may be segmented into a plurality of segments. Each of the ultrasound images may represent a boundary of the prostate as a feature. The AI model 125 may obtain a feature vector from each of a plurality of segmented ultrasound images by using a CNN According to an embodiment, the AI model 125 may be trained to identify a boundary of the object as a feature. Furthermore, the AI model 125 may be trained to obtain an object outline map image based on the identified outline of the object.

For example, the AI model 125 may identify a boundary of the object (e.g., the prostate) in the ultrasound image 510 applied to the AI model 125, based on feature vectors obtained from pieces of training data. The AI model 125 may obtain feature vectors by segmenting the ultrasound image 510 and identify the boundary of the object based on the obtained feature vector. The AI model 125 may obtain an object outline map image 530 from the ultrasound image 510, based on the identified outline of the object.

According to an embodiment, the AI model 125 may be trained to obtain, as a feature, Euclidean distance used in semantic segmentation that classifies an ultrasound image in a pixel-wise manner.

For example, the AI model 125 may obtain Euclidean distance away from the boundary of the object to each image pixel. The AI model 125 may obtain a distance map image 550 representing Euclidean distance away from the boundary of the object. The AI model 125 may generate the distance map image 550 by color-coding a region having equal Euclidean distance from the boundary of the object with the same color.

Figure 6:
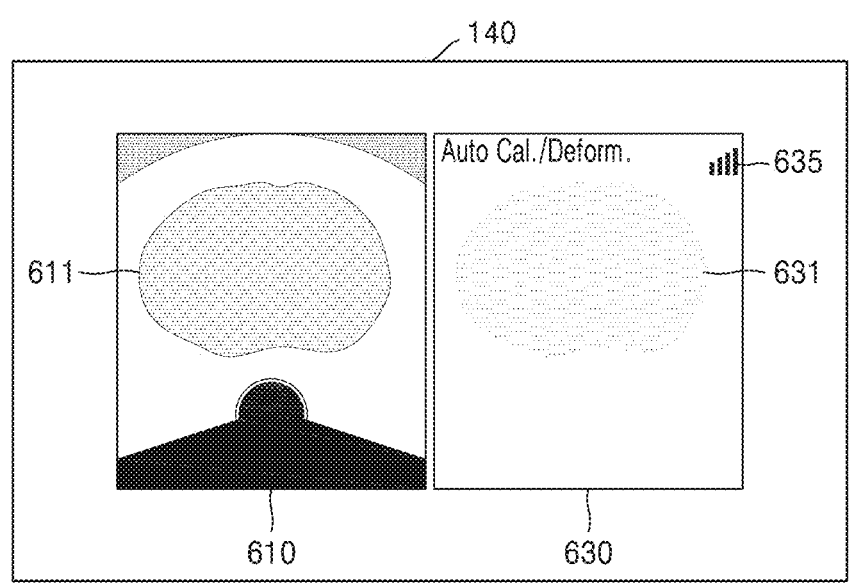
FIG. 6 illustrates an example in which a medical image displaying apparatus displays information regarding whether a condition for image registration is satisfied, according to an embodiment.
Figure 7:
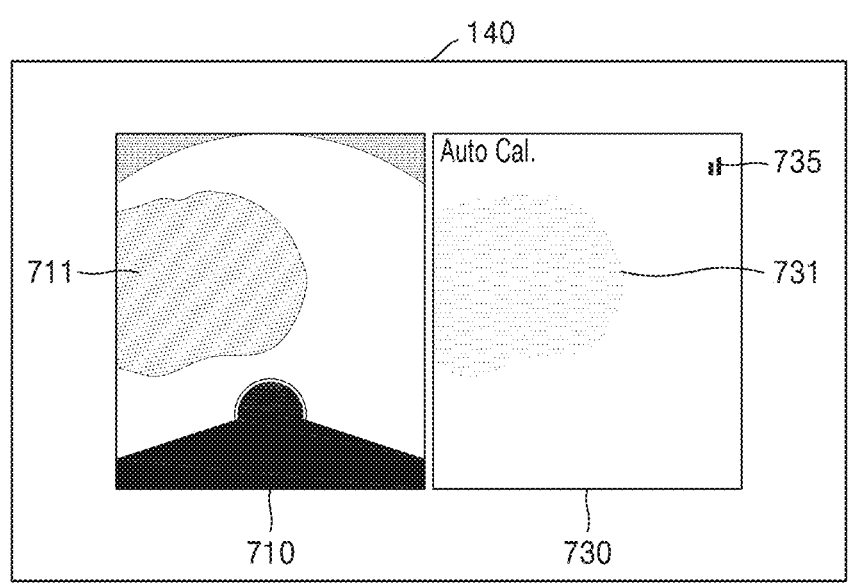
FIG. 7 illustrates an example in which a medical image displaying apparatus displays information regarding whether a condition for image registration is satisfied, according to an embodiment.

FIGS. 6 and 7 respectively illustrate examples in which a medical image displaying apparatus displays information regarding whether conditions for image registration are satisfied, according to embodiments.

Referring to FIGS. 6 and 7, the medical image displaying apparatus may respectively display, on a display 140, a pair of an ultrasound image 610 including an object 611 and a medical image 630 including an object 631 and a pair of an ultrasound image 710 including an object 711 and a medical image 730 including an object 731. Furthermore, the medical image displaying apparatus may display information regarding whether a condition for performing image registration between the pair of ultrasound image 610 and medical image 630 or the pair of ultrasound image 710 and medical image 730 is satisfied by using various methods.

Positions of the objects 611 and 711 in the ultrasound images 610 and 710 change depending on a direction in which an ultrasound signal transmitted by an ultrasound probe is oriented.

When the ultrasound image 610 of FIG. 6 is compared with the ultrasound image 710 of FIG. 7, the object 611 shown in FIG. 6 is entirely included in the ultrasound image 610, while only a part of the object 711 shown in FIG. 7 is included in the ultrasound image 710. In other words, the object 711 of FIG. 7 is partially outside the ultrasound image 710. As the objects 611 and 711 respectively fall partially outside the ultrasound images 610 and 710 to a greater extent, the accuracy of image registration decreases.

According to an embodiment, the medical image displaying apparatus may identify whether outlines of the objects 611 and 711 identified using the AI model 125 are entirely included in the ultrasound images 610 and 710, respectively. In other words, the medical image displaying apparatus may identify the extent to which the objects 611 and 711 fall outside the ultrasound images 610 and 710, respectively.

For example, the medical image displaying apparatus may respectively identify areas of the objects 611 and 711 in the ultrasound images 610 and 710 based on the boundaries of the objects 611 and 711 identified using the AI model 125. The medical image displaying apparatus may identify the extents to which the objects 611 and 711 are respectively included in the ultrasound images 610 and 710 based on the areas of the objects 611 and 711 in the ultrasound images 610 and 710.

In detail, the medical image displaying apparatus may identify the entire area of the object 611 in the ultrasound image 610 entirely including the object 611. The medical image displaying apparatus may identify the area of the object 711 in the ultrasound image 710 including only the part of the object 711. The medical image displaying apparatus may obtain a proportion of the area of the object 711 included in the ultrasound image 710 with respect to the entire area of the object 711. The medical image displaying apparatus may identify the extent to which the object 711 is included in the ultrasound image 710 based on the obtained proportion.

As another example, the medical image displaying apparatus may respectively determine positions of the objects 611 and 711 in the ultrasound images 610 and 710 based on the boundaries of the objects 611 and 711 identified using the AI model 125. The medical image displaying apparatus may identify the extents to which the objects 611 and 711 are respectively included in the ultrasound images 610 and 710 based on the positions of the objects 611 and 711 in the ultrasound images 610 and 710.

According to an embodiment, the medical image displaying apparatus may identify whether a condition for performing image registration is satisfied by comparing the extent to which an object is included in an ultrasound image with a preset threshold. For example, when the proportion of the area of the object 711 included in the ultrasound image 710 with respect to the entire area of the object 711 is less than 50%, the medical image displaying apparatus may identify that the condition for performing image registration is not satisfied.

According to an embodiment, the medical image displaying apparatus may identify whether a condition for performing image registration is satisfied based on information about a position of the probe 20 obtained using the sensor. For example, the medical image displaying apparatus may track movement of the probe 20 by using an electromagnetic sensor within a certain range of magnetic field generated by a magnetic field generator to thereby identify the extents to which the objects 611 and 711 respectively fall outside the ultrasound images 610 and 710.

According to an embodiment, the medical image displaying apparatus may display information indicating that the condition for performing image registration is not satisfied. For example, the medical image displaying apparatus may display a notification indicating that the object 711 falls outside the ultrasound image 710.

According to an embodiment, the medical image displaying apparatus may obtain information about reliability of image registration by comparing the extent to which an object is included in an ultrasound image with a preset threshold. The medical image displaying apparatus may display the information about the reliability of image registration.

For example, the medical image displaying apparatus may display information about the reliability of image registration by displaying bar graphs 635 and 735 respectively corresponding to preset thresholds on the display 140.

In detail, the medical image displaying apparatus may display, as the bar graph 735, a result of comparing the proportion of the area of the object 711 included in the ultrasound image 710 with respect to the entire area of the object 711 with a threshold set to 30%, 50%, or 70%.

Figure 8:
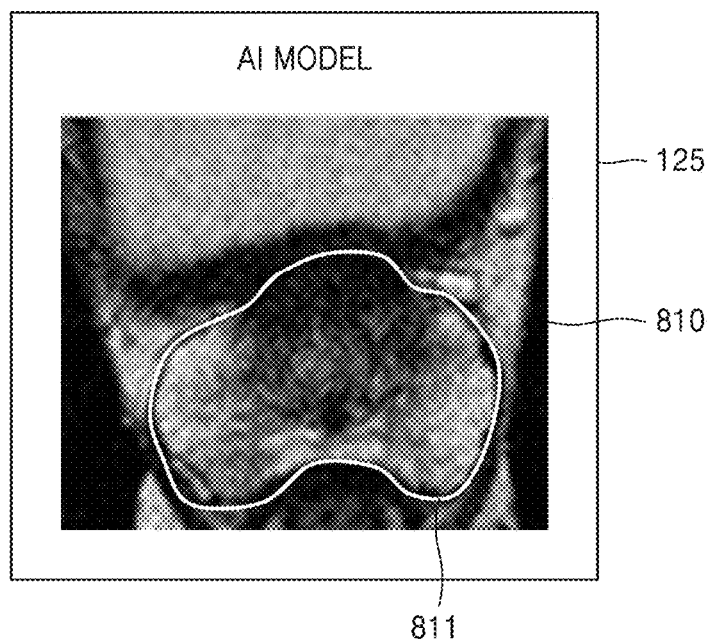
FIG. 8 illustrates an example in which a medical image displaying apparatus identifies whether a condition for image registration is satisfied, according to an embodiment.

FIG. 8 illustrates an example in which a medical image displaying apparatus identifies whether a condition for image registration is satisfied, according to an embodiment.

When an object 811 in an ultrasound image 810 is excessively small or large, a condition for performing image registration may not be satisfied.

Thus, referring to FIG. 8, the medical image displaying apparatus may identify whether a condition for performing image registration is satisfied based on a proportion of the object 811 occupying the ultrasound image 810.

According to an embodiment, the medical image displaying apparatus may obtain the proportion of the object 811 occupying the ultrasound image 810 based on a boundary of the object 811 identified using the AI model 125.

For example, the medical image displaying apparatus may identify an area of the object 811 in the ultrasound image 810 based on the boundary of the object 811 identified using the AI model 125. The medical image displaying apparatus may obtain the proportion of the object 811 occupying the ultrasound image 810 based on the area of the object 811.

According to an embodiment, the medical image displaying apparatus may identify whether the condition for performing image registration is satisfied by comparing the proportion of the object 811 occupying the ultrasound image 810 with a preset threshold.

For example, when the proportion of the object 811 occupying the ultrasound image 810 is less than 20%, the medical image displaying apparatus may identify that the condition for performing image registration is not satisfied.

As another example, when the proportion of the object 811 occupying the ultrasound image 810 is 90% or more, the medical image displaying apparatus may identify that the condition for performing image registration is not satisfied.

According to an embodiment, the medical image displaying apparatus may display information indicating that the condition for performing image registration is not satisfied. For example, the medical image displaying apparatus may display a notification indicating that the object 811 in the ultrasound image 811 is excessively small or large.

According to an embodiment, the medical image displaying apparatus may obtain information about reliability of image registration by comparing the proportion of the object 811 occupying the ultrasound image 810 with the preset threshold. The medical image displaying apparatus may display the information about the reliability of image registration.

Figure 9:
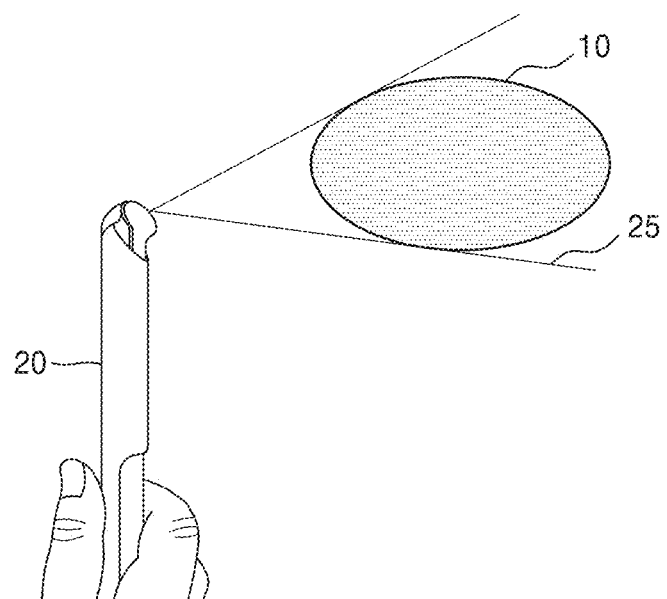
FIG. 9 illustrates an example in which a medical image displaying apparatus identifies whether a condition for image registration is satisfied, according to an embodiment.

FIG. 9 illustrates an example in which a medical image displaying apparatus identifies whether a condition for image registration is satisfied, according to an embodiment.

When a direction 25 in which an ultrasound signal transmitted from a probe 20 is oriented is not toward an object 10, image registration is difficult to perform.

Thus, referring to FIG. 9, the medical image displaying apparatus may identify whether a condition for performing image registration is satisfied based on the direction 25 in which the ultrasound signal transmitted from the probe 20 is oriented.

According to an embodiment, the medical image displaying apparatus may identify whether the condition for performing image registration is satisfied by identifying the direction 25 in which the ultrasound signal transmitted from the probe 20 is oriented based on information about the position of the probe 20 obtained via a sensor.

For example, the medical image displaying apparatus may identify the direction 25 in which the ultrasound signal transmitted from the probe 20 is oriented by tracking movement of the probe 20 via the electromagnetic sensor in a certain range of magnetic field generated by the magnetic field generator.

According to an embodiment, the medical image displaying apparatus may identify the direction 25 in which the ultrasound signal transmitted from the probe 20 is oriented, based on a boundary of the object 10 that is identified in an ultrasound image by using the AI model 125.

For example, the medical image displaying apparatus may identify a position of the object 10 in the ultrasound image based on the boundary of the object 10 identified using the AI model 125. The medical image displaying apparatus may identify the direction 25 in which the ultrasound signal transmitted from the probe 20 is oriented, based on the position of the object 10 in the ultrasound image.

According to an embodiment, the medical image displaying apparatus may display information indicating that the condition for performing image registration is not satisfied. For example, the medical image displaying apparatus may display information indicating that the direction 25 in which the ultrasound signal transmitted from the probe 20 is oriented is not toward the object 10.

Figure 10:
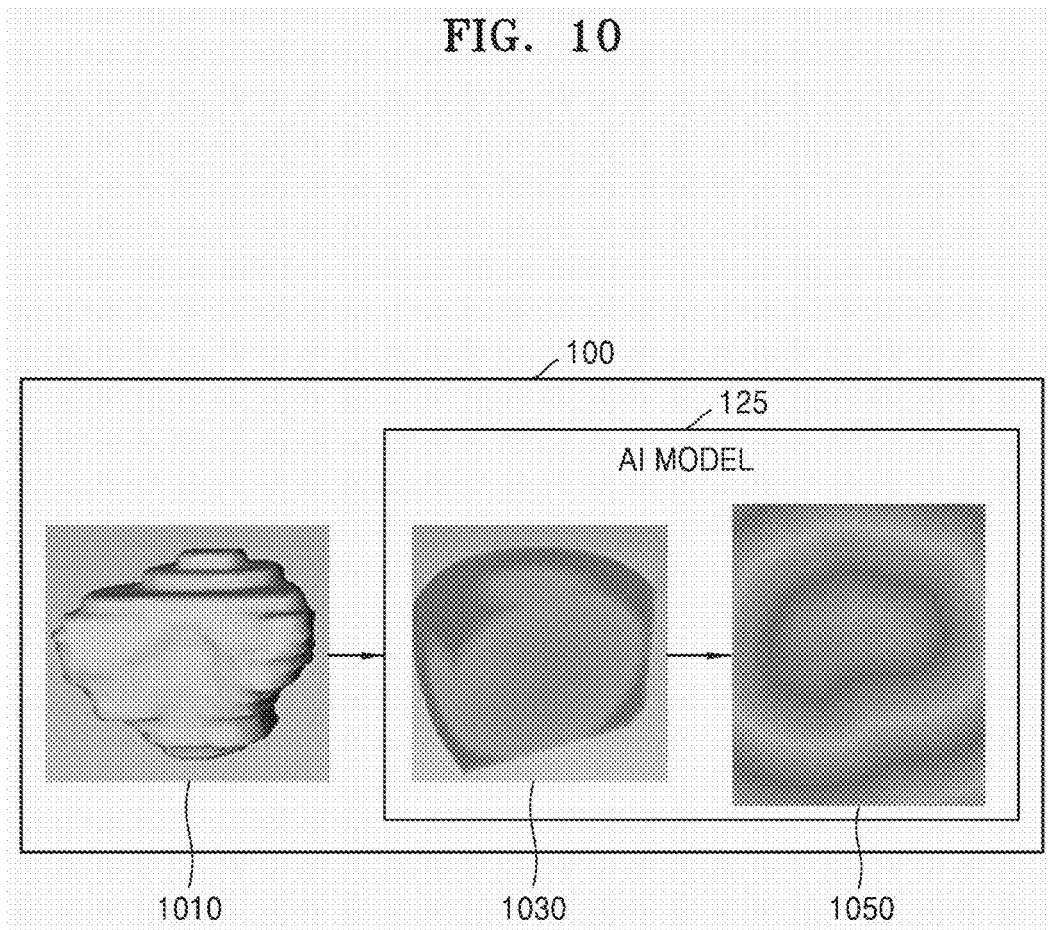
FIG. 10 illustrates an example in which a medical image displaying apparatus applies a medical image to an AI model, according to an embodiment.

FIG. 10 illustrates an example in which a medical image displaying apparatus applies a medical image to an AI model, according to an embodiment.

Referring to FIG. 10, the medical image displaying apparatus may apply a medical image 1010 to the AI model 125.

According to an embodiment, the AI model 125 may be built in the medical image displaying apparatus. Alternatively, the AI model 125 may be built on a server connected to the medical image displaying apparatus via a network. An embodiment in which the AI model 125 is built in the medical image displaying apparatus is described for convenience. It is obvious to those of ordinary skill in the art that details of the AI model 125 described below may be analogically applied to an AI model of other embodiments of the disclosure.

According to an embodiment, the medical image 1010 may be at least one of a CT image, an MR image, and a 3D ultrasound image.

According to an embodiment, the AI model 125 may be trained to obtain features from a medical image by learning a plurality of medical images, each including an object, as training data.

For example, a plurality of medical images, each including the prostate, may be input to the AI model 125 as training data. Each of the medical images may include a slice image. The slice image may be segmented into a plurality of segments. Each of the medical images may represent a boundary of the prostate as a feature. The AI model 125 may obtain a feature vector from each of a plurality of segmented cross-sectional medical images by using a CNN.

According to an embodiment, the AI model 125 may be trained to identify a boundary of the object as a feature. For example, the AI model 125 may be trained to identify a boundary of the object in a 3D medical image as a feature. As another example, the AI model 125 may be trained to identify a boundary of the object in a cross-sectional image as a feature.

Furthermore, the AI model 125 may be trained to obtain an object outline map image based on the identified outline of the object.

For example, the AI model 125 may identify a boundary of the object (e.g., the prostate) in the medical image 1010 applied to the AI model 125, based on feature vectors obtained from pieces of training data. The AI model 125 may obtain feature vectors by segmenting the medical image 1010 and identify the boundary of the object based on the obtained feature vector. The AI model 125 may obtain an object outline map image from the medical image 1010, based on the identified outline of the object.

According to an embodiment, the AI model 125 may be trained to obtain, as a feature, Euclidean distance used in semantic segmentation that classifies an ultrasound image in a pixel-wise manner.

For example, the AI model 125 may obtain Euclidean distance away from the boundary of the object. The AI model 125 may obtain a 3D distance map image 1030 representing Euclidean distance away from the boundary of the object. The AI model 125 may generate the 3D distance map image 1030 by color-coding a region having equal Euclidean distance from the boundary of the object with the same color.

According to an embodiment, the AI model 125 may generate a cross-sectional distance map image 1050 by slicing the 3D distance map image 1030.

For example, the AI model 125 may generate the cross-sectional distance map image 1050 by slicing the 3D distance map image 1030 based on information about the position of a probe.

According to an embodiment, features in the medical image 1010 may be previously obtained. For example, the features in the medical image 1010 may be obtained by an AI neural network built in a server from the medical image 1010 that is previously obtained and then may be transmitted to the medical image displaying apparatus. As another example, the features in the medical image 1010 may be obtained by an AI neural network built in the medical image displaying apparatus from the medical image 1010 that is previously obtained.

Figure 11:
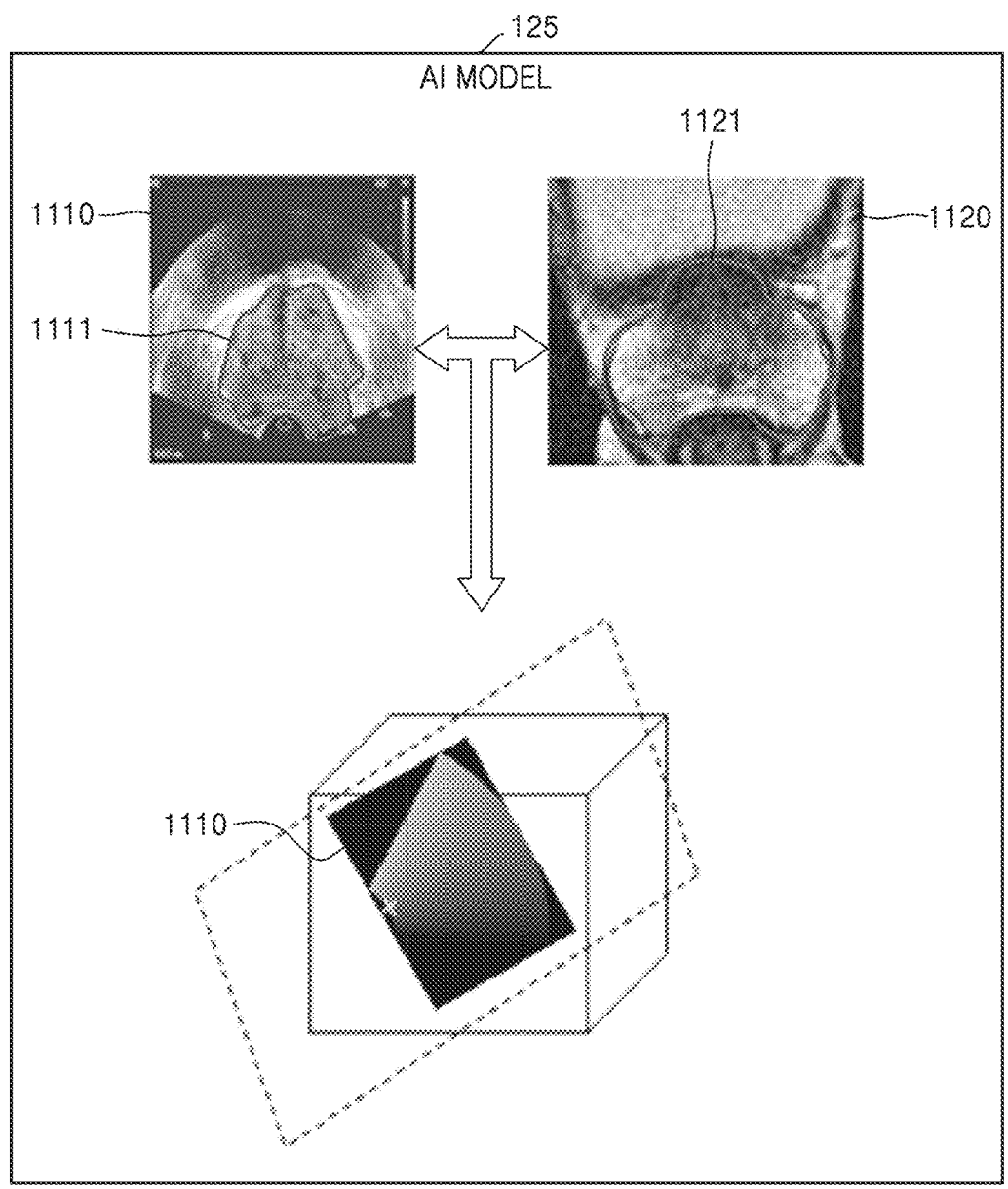
FIG. 11 illustrates an example in which a medical image displaying apparatus performs image registration between an ultrasound image and a medical image, according to an embodiment.

FIG. 11 illustrates an example in which a medical image displaying apparatus performs image registration between an ultrasound image and a medical image, according to an embodiment.

Referring to FIG. 11, the medical image displaying apparatus may perform image registration between an ultrasound image 1110 and a medical image 1120 by using the AI model 125.

According to an embodiment, the medical image displaying apparatus may perform image registration between a 3D ultrasound image and a 3D medical image.

According to an embodiment, the medical image displaying apparatus may perform image registration between a 2D ultrasound image and a cross-sectional image generated by slicing a 3D medical image. For example, the medical image displaying apparatus may extract a cross-sectional image from a 3D medical image based on information about the position of the probe 20 obtained via a sensor. The medical image displaying apparatus may perform image registration between a selected cross-sectional image and the 2D ultrasound image.

According to an embodiment, image registration performed by the AI model 125 between the ultrasound image 1110 and the medical image 1120 may be divided into two stages.

For example, the AI model 125 may perform overall registration between the ultrasound image 1110 and the medical image 1120 (stage 1 image registration) and then precise registration between an object 1111 in the ultrasound image 1110 and an object 1121 in the medical image 1120 (stage 2 image registration).

According to an embodiment, the AI model 125 may perform image registration between the ultrasound image 1110 and the medical image 1120 by comparing and matching features from the ultrasound image 1110 with corresponding features from the medical image 1120.

For example, the AI model 125 may perform image registration between the ultrasound image 1110 and the medical image 1120 by comparing and matching locations of features from the ultrasound image 1110 with those of corresponding features from the medical image 1120.

As another example, the AI model 125 may perform image registration between the ultrasound image 1110 and the medical image 1120 by comparing and matching a boundary of the object 1111 in the ultrasound image 1110 with a boundary of the object 1121 in the medical image 1120.

As another example, the AI model 125 may perform image registration between the ultrasound image 1110 and the medical image 1120 by comparing and matching a distance map image of the object 1111 from the ultrasound image 1110 with a distance map image of the object 1121 from the medical image 1120.

According to an embodiment, the AI model 125 may perform image registration between the ultrasound image 1110 and the medical image 1120 by rotating at least one of the ultrasound image 1110 and the medical image 1120 in order to compare and match features from the ultrasound image 1110 with corresponding features from the medical image 1120.

For example, the AI model 125 may rotate at least one of the ultrasound image 1110 and the medical image 1120 to perform overall image registration between the ultrasound image 1110 and the medical image 1120. The AI model 125 may rotate at least one of the ultrasound image 1110 and the medical image 1120 to match features of the object 1111 in the ultrasound image 1110 with corresponding features of the object 1121 in the medical image 1120.

According to an embodiment, the AI model 125 may perform a shape correction on at least one of the object 1111 in the ultrasound image 1110 and the object 1121 in the medical image 1120 by comparing and matching the features from the ultrasound image 1110 with the corresponding features from the medical image 1120.

For example, the AI model 125 may perform a shape correction on at least one of the object 1111 in the ultrasound image 1110 and the object 1121 in the medical image 1120 in order to precisely register the ultrasound image 1110 and the medical image 1120, as described in more detail below with reference to FIG. 12.

Figure 12:
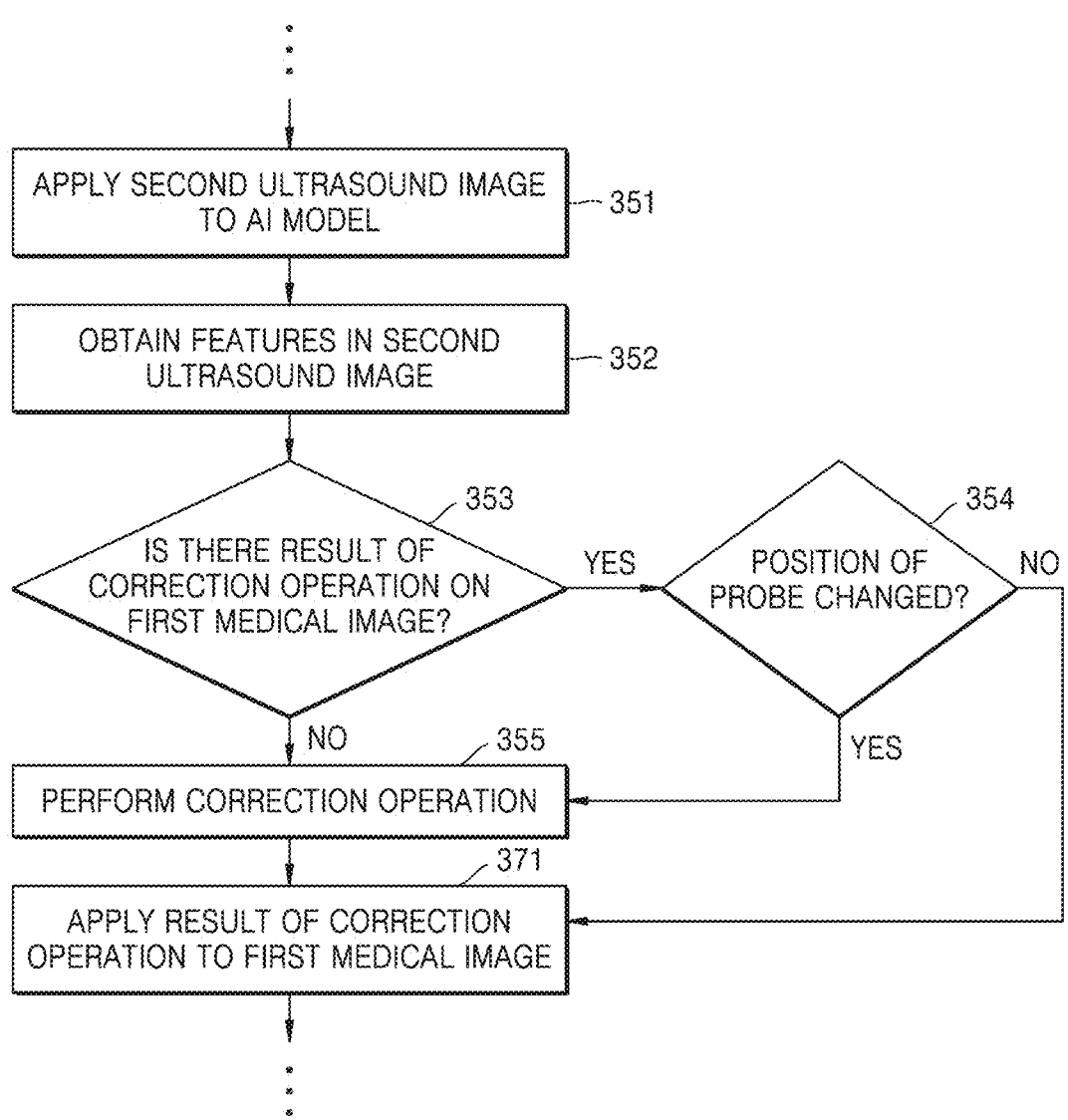
FIG. 12 is a flowchart of a method by which a medical image displaying apparatus applies a correction operation to a medical image, according to an embodiment.

FIG. 12 is a flowchart of a method by which a medical image displaying apparatus applies a correction operation to a medical image, according to an embodiment.

The medical image displaying apparatus may apply the second ultrasound image to the AI model 125 (operation 351). The second ultrasound image is an ultrasound image obtained in operation 350 of FIG. 3.

According to an embodiment, the second ultrasound image may be an ultrasound image newly obtained as the probe 20 moves. In this case, the medical image displaying apparatus may obtain the second ultrasound image in which a shape of an object is changed due to a pressure applied by the probe 20.

The AI model 125 may obtain features in the second ultrasound image (operation 352). The AI model 125 may output the obtained features in the second ultrasound image to the medical image displaying apparatus.

Because operation 352 is similar to operation 333 described with reference to FIG. 4, a repeated description thereof will be omitted here.

The medical image displaying apparatus may identify whether there is a result of performing a correction operation on the first medical image (operation 353).

According to an embodiment, the medical image may identify whether there is a result of performing a correction operation for changing a shape of the object in the first medical image via the AI model 125.

The medical image displaying apparatus may not perform an additional correction operation by applying the result of performing the correction operation on the first medical image to the first medical image. Thus, the medical image displaying apparatus may quickly perform image registration and display a resulting of applying a shape correction to the first medical image.

When there is a result of performing the correction operation on the first medical image, the medical image displaying apparatus may proceed to operation 354. On the other hand, when there is no result of performing the correction operation on the first medical image, the medical image displaying apparatus may proceed to operation 355.

The medical image displaying apparatus may identify whether a position of the probe 20 has been changed (operation 354).

According to an embodiment, the medical image displaying apparatus may identify whether the position of the probe 20 has been changed based on information about the position of the probe 20 obtained via a sensor. For example, the medical image displaying apparatus may identify whether the position of the probe 20 has been changed by tracking movement of the probe 20 with an electromagnetic sensor in a certain range of magnetic field generated by a magnetic field generator.

When the position of the probe 20 is changed, the medical image displaying apparatus may proceed to operation 355. In addition, when the position of the probe 20 is not changed, the medical image displaying apparatus may proceed to operation 371.

In other words, when the position of the probe 20 is not changed, the medical image displaying apparatus proceed to operation 371, thereby quickly performing image registration and displaying a medical image to which a shape correction has been applied.

The medical image displaying apparatus may perform a correction operation for transforming the first medical image (operation 355).

According to an embodiment, the medical image displaying apparatus may perform a correction operation for transforming the first medical image by comparing and matching, via the AI model 125, the features in the second ultrasound image obtained in operation 352 with corresponding features in the first medical image.

For example, the AI model 125 may perform a correction operation to obtain a vector for correcting differences, each difference being between a location of each feature from the second ultrasound image and a location of its corresponding feature from the first medical image.

As another example, the AI model 125 may perform a correction operation to obtain a vector for correcting a difference between outlines of the object, which are respectively obtained from the second ultrasound image and the first medical image.

As another example, the AI model 125 may perform a correction operation to obtain a vector for correcting a difference between distance map images of the object, which are respectively obtained from the second ultrasound image and the first medical image.

The medical image displaying apparatus may obtain a second medical image by applying a result of the correction operation to the first medical image (operation 371).

According to an embodiment, the medical image displaying apparatus may apply the result of the correction operation performed in operation 355 to the first medical image by using the AI model 125 to thereby obtain a second medical image including the object to which the shape correction has been applied.

For example, the AI model 125 may obtain the second medical image including the object to which the shape correction has been applied by applying a vector for correcting differences to the first medical image, each difference being between a location of each feature from the second ultrasound image and a location of its corresponding feature from the first medical image.

As another example, the AI model 125 may obtain the second medical image including the object to which the shape correction has been applied by applying, to the first medical image, a vector for correcting a difference between outlines of the object, which are respectively obtained from the second ultrasound image and the first medical image.

As another example, the AI model 125 may obtain the second medical image including the object to which the shape correction has been applied by applying, to the first medical image, a vector for correcting a difference between distance map images of the object, which are respectively obtained from the second ultrasound image and the first medical image.

According to an embodiment, an AI neural network built in the medical image displaying apparatus may store the second medical image in a memory of the medical image displaying apparatus. As another example, an AI neural network built on a server may transmit the second medical image to the medical image displaying apparatus over a network.

Figure 13:
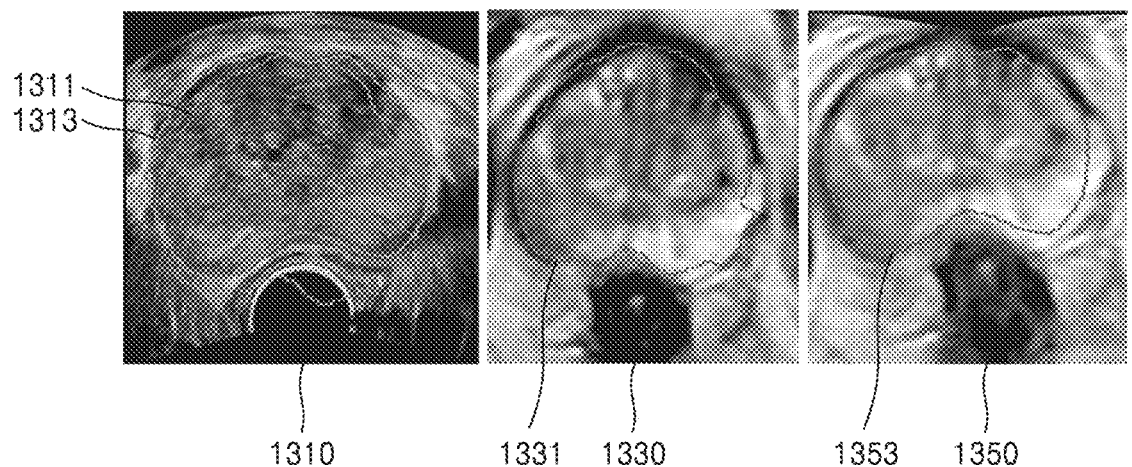
FIG. 13 illustrates a result obtained when a medical image displaying apparatus applies a result of a correction operation to a medical image, according to an embodiment.

FIG. 13 illustrates a result obtained when a medical image displaying apparatus applies a result of a correction operation to a medical image, according to an embodiment.

Referring to FIG. 13, an object 1311 is identified in the first ultrasound image obtained in operation 310 of FIG. 3. An object 1313 is identified in a second ultrasound image 1310 obtained in operation 350 of FIG. 3. An object 1331 is identified in a first medical image 1330 registered with the first ultrasound image in operation 330 of FIG. 3. An object 1353 is included in a second medical image 1350 obtained in operation 370 of FIG. 3.

When the first ultrasound image is registered with the first medical image 1330, the object 1311 in the first ultrasound image is matched to the object 1331 in the first medical image 1330. Thus, a shape of the object 1311 in the first ultrasound image is similar to a shape of the object 1331 in the first medical image 1330.

Furthermore, the object 1353 in the second medical image 1350 has a shape obtained by changing the shape of the object 1331 in the first medical image 1330 based on the object 1313 in the second ultrasound image 1310. Thus, the shape of the object 1313 in the second ultrasound image 1310 is similar to the shape of the object 1353 in the second medical image 1350.

According to experimental results, when the medical image displaying apparatus is a computer including an i7-4790 central processing unit (CPU) with 8 logical cores (running at 3.60 GHz), 16 gigabyte (GB) random access memory (RAM), and an Nvidia Quadro K2200 graphics processing unit (GPU), an average time of 115 ms per frame is required to correct a medical image. Thus, according to an embodiment of the disclosure, the medical image displaying apparatus may correct a medical image to correspond to an ultrasound image in real-time and display the resulting image.

Furthermore, the experimental results show that a result of correcting a medical image according to an embodiment of the disclosure has an error (an average trans-registration error for the Euclidean distance) of 1.595±1.602 mm in a phantom experiment while having an error (an average trans-registration error for the Euclidean distance) of 3.068±1.599 mm in a clinical experiment. Thus, the medical image displaying apparatus of the disclosed embodiment may correct a medical image registered with an ultrasound image to correspond to the ultrasound image and display a medical image to which a result of the correction has been applied, thereby clearly providing the user with information about an object.

Embodiments of the disclosure may be implemented through non-transitory computer-readable recording media having stored therein computer-executable instructions and data. The instructions may be stored in the form of program code, and when executed by a processor, generate a predefined program module to perform a preset operation. Furthermore, when executed by the processor, the instructions may perform preset operations according to embodiments.

What is claimed is:

1. A method of displaying a medical image by using a medical image displaying apparatus, the method comprising:

transmitting ultrasound signals to an object and receiving ultrasound echo signals from the object using an ultrasound probe of the medical image displaying apparatus;

obtaining a first ultrasound image based on the ultrasound echo signals;

identifying a first outline of the object included in the first ultrasound image as a feature of the first ultrasound image by applying the first ultrasound image to an artificial intelligence model;

identifying a second outline of the object included in a pre-obtained first medical image using the artificial intelligence model as a feature of the first medical image;

performing image registration between the first ultrasound image and the first medical image by matching the feature of the first ultrasound image and the feature of the first medical image;

obtaining a second ultrasound image of the object using the ultrasound probe;

obtaining a second medical image by transforming the first medical image to correspond to the second ultrasound image; and displaying the second medical image together with the second ultrasound image, wherein the performing of the image registration comprises:

obtaining a first proportion occupied by the object in the first ultrasound image based on the first outline of the object; and identifying whether a condition for image registration is satisfied based on whether the first proportion is less than or greater than a preset threshold.

2. The method of claim 1, wherein the performing of the image registration further comprises:

displaying information about a reliability of the image registration based on a result of the identifying whether the condition for image registration is satisfied.

3. The method of claim 1, wherein the identifying of whether the condition for the image registration is satisfied comprises:

obtaining, based on the feature of the first ultrasound image, a second proportion indicating a proportion of an area of the object included in the first ultrasound image with respect to an entire area of the object;

comparing the second proportion with another preset threshold; and identifying whether the condition for the image registration is satisfied based on a result of the comparing.

4. The method of claim 1, wherein the identifying of whether the condition for the image registration is satisfied comprises:

identifying a direction in which an ultrasound signal transmitted from the ultrasound probe is oriented; and identifying whether the condition for the image registration is satisfied based on the identified direction.

5. The method of claim 1, wherein the obtaining of the feature of the first ultrasound image comprises obtaining a first distance map indicating a distance from the first outline of the object to each pixel in the first ultrasound image, and wherein the matching of the feature of the first ultrasound image and the feature of the first medical image comprises comparing the first distance map with a second distance map previously obtained from the first medical image by using the artificial intelligence model.

6. The method of claim 5, wherein the first medical image is a three-dimensional medical image and the second distance map is a three-dimensional image representing a distance from a three-dimensional outline to each pixel in the first medical image that is obtained from the first medical image by using the artificial intelligence model, and wherein the comparing of the first distance map with the second distance map comprises:
  obtaining a third distance map that is a two-dimensional image by slicing the second distance map; and
  comparing the third distance map with the first distance map.

7. The method of claim 1, wherein the obtaining of the second ultrasound image comprises obtaining the second ultrasound image including the object that is deformed by pressing the object with the ultrasound probe, and
  wherein the obtaining of the second medical image comprises:
    obtaining a third outline of the object included in the second ultrasound image as a feature of the second ultrasound image by applying the second ultrasound image to the artificial intelligence model; and
    obtaining the second medical image by transforming the first medical image based on a result of the comparing of the feature of the first medical image with the feature of the second ultrasound image.

8. A medical image displaying apparatus comprising:
  a display;
  an ultrasound probe configured to transmit ultrasound signals to an object and receive ultrasound echo signals from the object;
  a memory storing one or more instructions; and
  a processor executing the one or more instructions and configured to:
    obtain a first ultrasound image based on the ultrasound echo signals;
    identify a first outline of the object included in the first ultrasound image as a feature of the first ultrasound image by applying the first ultrasound image to an artificial intelligence model;
    identifying a second outline of the object included in a pre-obtained first medical image using the artificial intelligence model as a feature of the first medical image;
    perform image registration between the first ultrasound image and the first medical image by matching the feature of the first ultrasound image and the feature of the first medical image;
  control the ultrasound probe to obtain a second ultrasound image of the object;
  obtain a second medical image by transforming the first medical image to correspond to the second ultrasound image; and
  control the display to display the second medical image together with the second ultrasound image,
  wherein the processor is further configured to:
    obtain a first proportion occupied by the object in the first ultrasound image based on the first outline of the object; and
    identify whether a condition for image registration is satisfied based on whether the first proportion is less than or greater than a preset threshold.

9. The medical image displaying apparatus of claim 8, wherein the processor is further configured to:
  control the display to display information about a reliability of the image registration based on a result of the identifying whether the condition for image registration is satisfied.

10. The medical image displaying apparatus of claim 8, wherein the processor is further configured to:
  obtain, based on the feature of the first ultrasound image, a second proportion indicating a proportion of an area of the object included in the first ultrasound image with respect to an entire area of the object;
  compare the second portion with a preset another preset threshold; and
  identify whether the condition for the image registration is satisfied based on a result of the comparing.

11. The medical image displaying apparatus of claim 8, wherein the processor is further configured to:
  identify a direction in which an ultrasound signal transmitted from the ultrasound probe is oriented; and
  identify whether the condition for the image registration is satisfied based on the identified direction.

12. The medical image displaying apparatus of claim 8, wherein the processor is further configured to:
  obtain a first distance map indicating a distance from the first outline of the object to each pixel in the first ultrasound image;
  compare the first distance map with a second distance map previously obtained from the first medical image by using the artificial intelligence model.

13. The medical image displaying apparatus of claim 12, wherein the first medical image is a three-dimensional medical image and the second distance map is a three-dimensional image representing a distance from a three-dimensional outline that is obtained from the first medical image to each pixel in the first ultrasound image by using the artificial intelligence model, and
  wherein the processor is further configured to:
    obtain a third distance map that is a two-dimensional image by slicing the second distance map; and
    compare the third distance map with the first distance map.

14. The medical image displaying apparatus of claim 8, wherein the processor is further configured to:
  obtain the second ultrasound image including the object that is deformed by pressing the object with the ultrasound probe;
  obtain a third outline of the object included in the second ultrasound image as a feature of the second ultrasound image by applying the second ultrasound image to the artificial intelligence model; and
  obtain the second medical image by transforming the first medical image based on a result of the comparing of the feature of the first medical image with the feature of the second ultrasound image.

* * * * *